(12) United States Patent
Revuelta et al.

(10) Patent No.: US 8,591,570 B2
(45) Date of Patent: Nov. 26, 2013

(54) PROSTHETIC HEART VALVE FOR REPLACING PREVIOUSLY IMPLANTED HEART VALVE

(75) Inventors: José M. Revuelta, Cantabria (ES); Jack D. Lemmon, St. Louis Park, MN (US); Timothy R. Ryan, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 546 days.

(21) Appl. No.: 12/048,725

(22) Filed: Mar. 14, 2008

(65) Prior Publication Data

US 2008/0161910 A1 Jul. 3, 2008

Related U.S. Application Data

(62) Division of application No. 10/935,730, filed on Sep. 7, 2004.

(51) Int. Cl.
*A61F 2/24* (2006.01)

(52) U.S. Cl.
USPC .......................................... 623/1.26; 623/2.12

(58) Field of Classification Search
USPC ..................... 623/1.16, 1.26, 2.11, 2.12–2.19
See application file for complete search history.

(56) References Cited

U.S. PATENT DOCUMENTS

| | | | |
|---|---|---|---|
| 3,334,629 A | 8/1967 | Cohn | |
| 3,409,013 A | 11/1968 | Berry | |
| 3,540,431 A | 11/1970 | Mobin-Uddin | |
| 3,587,115 A | 6/1971 | Shiley | |
| 3,628,535 A | 12/1971 | Ostrowsky et al. | |
| 3,642,004 A | 2/1972 | Osthagen et al. | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,035,849 A | 7/1977 | Angell et al. | |
| 4,056,854 A | 11/1977 | Boretos et al. | |
| 4,106,129 A | 8/1978 | Carpentier et al. | |

(Continued)

FOREIGN PATENT DOCUMENTS

| | | |
|---|---|---|
| DE | 195 32 846 | 3/1997 |
| DE | 195 46 692 | 6/1997 |

(Continued)

OTHER PUBLICATIONS

P. Bonhoeffer, MD, et al., "Transcatheter Implantation of a Bovine Valve in Pulmonary Position—A Lamb Study", pp. 813-816; Aug. 2000.

(Continued)

*Primary Examiner* — David Isabella
*Assistant Examiner* — Randy Shay

(57) ABSTRACT

A method of functionally replacing a previously implanted prosthetic heart valve. The method includes positioning a replacement prosthetic heart valve within an internal region defined by the previously implanted prosthetic heart valve. The replacement prosthetic heart valve is then physically docked to the previously implanted prosthetic heart valve. With this technique, the previously implanted prosthetic heart valve serves as a platform for securement of the replacement prosthetic heart valve to the patient's native tissue.

10 Claims, 13 Drawing Sheets

(56) References Cited

U.S. PATENT DOCUMENTS

| | | |
|---|---|---|
| 4,222,126 A | 9/1980 | Boretos et al. |
| 4,233,690 A | 11/1980 | Akins |
| 4,291,420 A | 9/1981 | Reul |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Stecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,156,621 A | 10/1992 | Navia et al. |
| 5,161,547 A | 11/1992 | Tower |
| 5,163,953 A | 11/1992 | Vince |
| 5,167,628 A | 12/1992 | Boyles |
| 5,197,979 A | 3/1993 | Quintero et al. |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A * | 7/1994 | Teitelbaum .................. 623/2.42 |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,480,424 A | 1/1996 | Cox |
| 5,489,294 A | 2/1996 | McVenes et al. |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,749,890 A | 5/1998 | Shaknovich |
| 5,766,151 A | 6/1998 | Valley et al. |
| 5,776,188 A * | 7/1998 | Shepherd et al. ............ 623/2.38 |
| 5,782,809 A | 7/1998 | Umeno et al. |
| 5,800,456 A | 9/1998 | Maeda et al. |
| 5,817,126 A | 10/1998 | Imran |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersent et al. |
| 5,855,597 A | 1/1999 | Jayaraman |
| 5,855,601 A | 1/1999 | Bessler et al. |
| 5,860,996 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,001,126 A | 12/1999 | Nguyen-Thien-Nhon |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,051,104 A | 4/2000 | Jang |
| 6,059,809 A | 5/2000 | Amor et al. |
| 6,110,201 A | 8/2000 | Quijano et al. |
| 6,123,723 A | 9/2000 | Konya et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,164,339 A | 12/2000 | Greenhalgh |
| 6,165,216 A | 12/2000 | Agathos |
| 6,168,614 B1 | 1/2001 | Andersen et al. |
| 6,171,335 B1 | 1/2001 | Wheatley et al. |
| 6,192,944 B1 | 2/2001 | Greenhalgh |
| 6,200,336 B1 | 3/2001 | Pavcnik et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,254,436 B1 | 7/2001 | Nitta et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,327,772 B1 | 12/2001 | Zadno-Azizi et al. |
| 6,338,735 B1 | 1/2002 | Stevens |
| 6,342,070 B1 | 1/2002 | Nguyen-Thien-Nhon |

(56) References Cited

U.S. PATENT DOCUMENTS

| | | |
|---|---|---|
| 6,348,063 B1 | 2/2002 | Yassour et al. |
| 6,350,282 B1 | 2/2002 | Eberhardt |
| 6,352,708 B1 | 3/2002 | Duran et al. |
| 6,364,905 B1 | 4/2002 | Simpson et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,509,930 B1 | 1/2003 | Hirano et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,558,417 B2 | 5/2003 | Peredo |
| 6,559,603 B2 | 5/2003 | Iwami |
| 6,562,058 B2 | 5/2003 | Seguin et al. |
| 6,569,196 B1 | 5/2003 | Vesely |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,622,604 B1 | 9/2003 | Chouinard et al. |
| 6,627,873 B2 | 9/2003 | Tchakarov et al. |
| 6,632,243 B1 | 10/2003 | Zadno-Azizi et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Streeter et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sleevers |
| 7,011,681 B2 | 3/2006 | Vesely |
| 7,041,128 B2 | 5/2006 | Mcguckin, Jr. et al. |
| 7,044,966 B2 | 5/2006 | Svanjdze et al. |
| 7,048,014 B2 | 5/2006 | Hyodoh et al. |
| 7,097,659 B2 | 8/2006 | Woolfson et al. |
| 7,115,141 B2 | 10/2006 | Menz et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,384,411 B1 | 6/2008 | Condado |
| 7,597,711 B2 | 10/2009 | Drews et al. |
| 7,806,927 B2 | 10/2010 | Styre |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044591 A1 | 11/2001 | Stevens et al. |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0077696 A1 | 6/2002 | Zadno-Azizi et al. |
| 2002/0095209 A1 | 7/2002 | Zadno-Azizi et al. |
| 2002/0111674 A1 | 8/2002 | Chouinard et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0069635 A1 | 4/2003 | Cartledge et al. |
| 2003/0109924 A1 | 6/2003 | Cribier |
| 2003/0125795 A1 | 7/2003 | Pavcnik et al. |
| 2003/0125805 A1 | 7/2003 | Johnson et al. |
| 2003/0130729 A1 | 7/2003 | Paniagua et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |

(56) References Cited

U.S. PATENT DOCUMENTS

| | | |
|---|---|---|
| 2003/0153974 A1 | 8/2003 | Spenser et al. |
| 2003/0181850 A1 | 9/2003 | Diamond et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Sequin et al. |
| 2004/0093075 A1 | 5/2004 | Kuehne |
| 2004/0097788 A1 | 5/2004 | Mourles et al. |
| 2004/0098112 A1 | 5/2004 | DiMatteo et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Laskinski et al. |
| 2004/0167573 A1 | 8/2004 | Williamson |
| 2004/0167620 A1 | 8/2004 | Ortiz |
| 2004/0186563 A1 | 9/2004 | Lobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0225355 A1 | 11/2004 | Stevens |
| 2004/0254636 A1 | 12/2004 | Flagle et al. |
| 2004/0260317 A1 | 12/2004 | Bloom et al. |
| 2004/0260394 A1 | 12/2004 | Douk et al. |
| 2004/0267357 A1 | 12/2004 | Allen et al. |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137682 A1* | 6/2005 | Justino ..................... 623/1.24 |
| 2005/0137686 A1 | 6/2005 | Salahieh |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0148997 A1 | 7/2005 | Valley et al. |
| 2005/0165477 A1 | 7/2005 | Anduiza et al. |
| 2005/0187616 A1 | 8/2005 | Realyvasquez |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0209065 A1 | 9/2005 | Schlosser |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0251251 A1 | 11/2005 | Cribier |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0247763 A1 | 11/2006 | Slater |
| 2006/0259134 A1 | 11/2006 | Schwammenthal et al. |
| 2006/0259137 A1 | 11/2006 | Artof et al. |
| 2006/0271081 A1 | 11/2006 | Realyvasquez |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0112415 A1 | 5/2007 | Barlett |
| 2007/0162102 A1 | 7/2007 | Ryan et al. |
| 2007/0162113 A1 | 7/2007 | Sharkawy et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |

(56) References Cited

U.S. PATENT DOCUMENTS

| | | | |
|---|---|---|---|
| 2007/0244557 | A1 | 10/2007 | Rafiee et al. |
| 2007/0250160 | A1 | 10/2007 | Rafiee |
| 2007/0255394 | A1 | 11/2007 | Ryan |
| 2007/0255396 | A1 | 11/2007 | Douk et al. |
| 2007/0288000 | A1 | 12/2007 | Bonan |
| 2008/0009940 | A1 | 1/2008 | Cribier |
| 2008/0015671 | A1 | 1/2008 | Bonhoeffer |
| 2008/0021552 | A1 | 1/2008 | Gabbay |
| 2008/0133003 | A1 | 6/2008 | Seguin et al. |
| 2008/0147105 | A1 | 6/2008 | Wilson et al. |
| 2008/0154356 | A1 | 6/2008 | Obermiller et al. |
| 2008/0161910 | A1 | 7/2008 | Revuelta et al. |
| 2008/0161911 | A1 | 7/2008 | Revuelta et al. |
| 2008/0183273 | A1 | 7/2008 | Mesana et al. |
| 2008/0215144 | A1 | 9/2008 | Ryan et al. |

FOREIGN PATENT DOCUMENTS

| | | | |
|---|---|---|---|
| DE | 198 57 887 | | 7/2000 |
| DE | 199 07 646 | | 8/2000 |
| DE | 10049812 | | 4/2002 |
| DE | 10049813 | | 4/2002 |
| DE | 10049815 | | 4/2002 |
| EP | 1057460 | A1 | 6/2000 |
| EP | 1057459 | | 12/2000 |
| EP | 1088529 | | 4/2001 |
| EP | 0937439 | B1 | 9/2003 |
| EP | 1340473 | | 9/2003 |
| EP | 1356793 | | 10/2003 |
| EP | 0819013 | | 6/2004 |
| EP | 1229864 | B1 | 4/2005 |
| FR | 2788217 | | 12/1999 |
| FR | 2 826 863 | | 1/2003 |
| SU | 1271508 | | 11/1986 |
| WO | WO 93/15693 | | 8/1993 |
| WO | WO 95/04556 | | 2/1995 |
| WO | WO 95/29640 | | 11/1995 |
| WO | WO 96/14032 | | 5/1996 |
| WO | WO 98/36790 | | 8/1998 |
| WO | WO 00/09059 | | 2/2000 |
| WO | 00/41652 | | 7/2000 |
| WO | 00/47136 | | 8/2000 |
| WO | WO 00/44308 | | 8/2000 |
| WO | WO 00/44313 | | 8/2000 |
| WO | WO 00/67661 | | 11/2000 |
| WO | WO 01/05331 | | 1/2001 |
| WO | WO 01/35870 | | 5/2001 |
| WO | WO 01/64137 | | 9/2001 |
| WO | 02/41789 | | 5/2002 |
| WO | WO 02/36048 | | 5/2002 |
| WO | WO 02/100297 | | 12/2002 |
| WO | WO 03/003943 | | 1/2003 |
| WO | WO 03/003949 | * | 1/2003 |
| WO | WO 03/011195 | | 2/2003 |
| WO | WO 03/015851 | | 11/2003 |
| WO | 2004/019825 | | 3/2004 |
| WO | WO 2004/019811 | | 3/2004 |
| WO | WO 2004/023980 | | 3/2004 |
| WO | WO 2004/041126 | | 5/2004 |
| WO | WO 2004/047681 | | 6/2004 |
| WO | 2005/004753 | | 1/2005 |
| WO | WO 2005/013860 | | 2/2005 |
| WO | 2005072655 | | 8/2005 |
| WO | 2006027500 | | 3/2006 |
| WO | 2008/100599 | | 8/2008 |

OTHER PUBLICATIONS

P. Bonhoeffer, MD, et al., "Percutaneous Replacement of Pulmonary Valve in a Right-Ventricle to Pulmonary-Artery Prosthetic Conduit with Valve Dysfunction", pp. 1403-1405; Oct. 2000.

Y. Boudjemline, MD, et al., "Steps Towards Percutaneous Aortic Valve Replacement", pp. 775-778; Feb. 2002.

P. Bonhoeffer, MD, et al., "Percutaneous Insertion of the Pulmonary Valve", Journal of the American College of Cardiology, vol. 39, No. 10, pp. 1664-1669; Feb. 2002.

A. Cribier, MD, et al, "PercutaneousTranscatheter Implantation of an Aortic Valve Prosthesis for Calcific Aortic Stenosis—First Human Description", pp. 3006-3008; Dec. 2002.

A. Cribier, MD, et al., "Early Experience with Percutaneous Transcatheter Implantation of Heart Valve Prosthesis for the Treatment of End-Stage Inoperable Patients with Calcific Aortic Stenosis", Journal of the American College of Cardiology, vol. 43, No. 4, pp. 698-703; Nov. 2003.

Y. Boudjemline, MD, et al., "Percutaneous Pulmonary Valve Replacement in a Large Right Ventricular Outflow Tract", Journal of the American College of Cardiology, vol. 43, No. 6; pp. 1082-1087; Mar. 2004.

Bonhoeffer, "Percutaneous insertion of the pulmonary valve," Journal of American College of Cardiology Foundation, (2002) 39(10):1664-1669.

Iliopoulos, et al., "Repeat replacement of aortic valve bioprosthesis," Ann. Thorac. Surg., (1995), 59:1217-1219.

Andersen, H.R. et al, "Transluminal implantation of artificial heart valves. Description of a new expandable aortic valve and initial results with implantation by catheter technique in closed chest pigs." Euro. Heart J. (1992) 13:704-708.

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.

Bonhoeffer, et al, "Technique and Results of Percutaneous Mitral Valvuloplasty With the Multi-Track System," Journal of Interventional Cardiology (United States), 200, pp. 263-268.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Valve Insertion: A New Approach," Journal of Thoracic and Cardiovascular Surgery (United States), Mar. 2003, pp. 741-742.

(56) References Cited

OTHER PUBLICATIONS

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," EuroIntervention Supplements (2006), 1 (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. IV-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Yonga, et al, "Effect of Percutaneous Balloon Mitral Valvotomy on Pulmonary Venous Flow in Severe Mitral Stenosis," East African Medical Journal (Kenya), Jan. 1999, pp. 28-30.

Yonga, et al, "Percutaneous Balloon Mitral Valvotomy: Initial Experience in Nairobi Using a New Multi-Track Catheter System," East African Medical Journal (Kenya), Feb. 1999, pp. 71-74.

Yonga, et al, "Percutaneous Transluminal Balloon Valvuloplasty for Pulmonary Valve Stenosis: Report on Six Cases," East African Medical Journal (Kenya), Apr. 1994, pp. 232-235.

Yonga, et al, "Percutaneous Transvenous Mitral Commissurotomy in Juvenile Mitral Stenosis," East African Medical Journal (Kenya), Apr. 2003, pp. 172-174.

European Search Report mailed Aug. 13, 2013 in corresponding EP Appln No. 12 15 5264.

* cited by examiner

PROSTHETIC HEART VALVE FOR REPLACING PREVIOUSLY IMPLANTED HEART VALVE

CROSS-REFERENCE TO RELATED APPLICATIONS

This application is a divisional application of U.S. patent application Ser. No. 10/935,730 filed on Sep. 7, 2004.

BACKGROUND

The present invention relates to prosthetic heart valves. More particularly, it relates to a device and method for functionally replacing a deficient, previously implanted prosthetic heart valve.

Implantable heart valve prostheses have long been used to replace various diseased or damaged natural aortic valves, mitral valves, pulmonic valves, and tricuspid valves of the heart. The actual shape and configuration of any particular prosthetic heart valve is, of course, dependent upon the valve being replaced. Generally, the known heart valve prostheses are either bioprostheses or mechanical heart valve prostheses. The bioprostheses or "tissue valves" are generally made of a suitable animal tissue or materials (e.g., harvested porcine valve leaflets, bovine or equine pericardial leaflets, synthetic material leaflets, etc.) that may be mounted onto a stationary metal or plastic frame, referred to as a "stent". Regardless of whether a stent is provided, bioprosthetic/synthetic heart valves are generally tubular (i.e., when the leaflets are "open", an internal passage is defined through which fluid (e.g., blood) can flow), and include a sewing or suture ring.

The sewing or suture ring provides a means for fixing the prosthetic heart valve to the patient's native heart valve orifice tissue (e.g., native annulus or valvular rim) associated with the native heart valve being repaired or replaced. In particular, an exacting surgical implantation technique is traditionally employed whereby the heart is stopped (cardiopulmonary bypass) and opened followed by surgical removal of damaged or diseased natural valve structure. Subsequently, the prosthetic heart valve is properly oriented within the native valvular area, with the sewing ring being seated against or at the native annulus or valvular rim. Sutures are then used to affix the sewing ring to the natural tissue.

A successfully implanted prosthetic heart valve will normally function without problem for many years. In certain instances, however, deficiencies may become evident shortly after implant or within a few years (especially in younger patients). Common functional deficiencies relate to calcification of the prosthetic heart valve leaflets, stenosis, and prosthetic heart valve insufficiency.

Under these and other circumstances, the prosthetic heart valve does not function properly, or no longer functions properly, and conventionally is surgically removed and replaced. Removal of a previously implanted prosthetic heart valve entails the same surgical intervention described above, coupled with the need to implant a new prosthetic heart valve. As a point of reference, while well-accepted, the conventional surgical intervention described above is difficult to perform and can result in patient injury or more severe complications. In fact, due to physical weakness, implantation of a prosthetic heart valve via the conventional surgical technique may be considered either too high risk or contra-indicated for certain patients. Further, removal of a previously implanted prosthetic heart valve requires cutting of the sutures that otherwise secure the prosthesis to the native annulus/valvular rim, and re-stitching of a new sewing ring. These activities can further compromise the integrity of the valvular rim and lead to recovery complications, morbidity and mortality.

Percutaneously-delivered prosthetic heart valves have been suggested having a generally similar configuration, such as by Bonhoeffer, P. et al., "Transcatheter Implantation of a Bovine Valve in Pulmonary Position." Circulation, 2002; 102:813-816 and Cribier, A. et al. "Percutaneous Transcatheter Implantation of an Aortic Valve Prosthesis for Calcific Aortic Stenosis." Circulation, 2002; 106:3006-3008, the teachings of which are incorporated herein by reference. These techniques appear to rely upon a frictional engagement between the expanded support structure and the native tissue to maintain a position of the delivered prosthesis. That is to say, with the transcatheter technique, conventional sewing of the prosthetic heart valve to the patient's native tissue cannot be performed. Similarly, Bonhoeffer, P. et al., "Percutaneous Insertion of the Pulmonary Valve." J Am Coll Cardiol, 2002; 39:1664-1669, the teachings of which are incorporated herein by reference, describe percutaneous delivery of a biological valve, sutured to an expandable stent, within a previously implanted valved or non-valved conduit, or a previously implanted valve. Again, it appears that radial expansion of the secondary valve stent is the sole means for placing and maintaining the replacement valve.

Prosthetic heart valves continue to be essential tools in the treatment of patient's suffering from cardiac deficiencies. Further, the investigation into percutaneously-delivered prosthetic heart valves appears promising. Unfortunately, the inability to rigidly affix a percutaneous prosthetic heart valve remains problematic. Therefore, a need exists for a prosthetic heart valve and related method of implant that is conducive to percutaneous delivery for replacing a deficient, previously implanted prosthetic heart valve.

SUMMARY

One aspect of the present invention relates to a method of functionally replacing a previously implanted prosthetic heart valve. The method includes positioning a replacement prosthetic heart valve within an internal region defined by the previously implanted prosthetic heart valve. The replacement prosthetic heart valve is then physically docked to the previously implanted prosthetic heart valve. With this technique, the previously implanted prosthetic heart valve serves as a platform for securement of the replacement prosthetic heart valve to the patient's native tissue.

Another aspect of the present invention relates to a prosthetic heart valve for functionally replacing a previously implanted prosthetic heart valve. The prosthetic heart valve includes a support structure, leaflets, and coupling means. The leaflets are mounted to the support structure. The coupling means is associated with the support structure and is adapted to physically dock the prosthetic heart valve to a previously implanted prosthetic heart valve.

Another aspect of the present invention relates to a prosthetic heart valve comprising a support structure, leaflets, and connection means. The leaflets are mounted to the support structure. The connection means is associated with the support structure and is adapted to effectuate physical docking of a replacement prosthetic heart valve to the prosthetic heart valve.

Another aspect of the present invention relates to a prosthetic heart valve system comprising a first prosthetic heart valve and a replacement heart valve. The first prosthetic heart valve is configured for initial implantation to native heart tissue and includes a support structure, leaflets, and connection means. The leaflets are mounted to the support structure and the connection means is associated with the support structure. The replacement prosthetic heart valve includes a support structure, leaflets, and coupling means. The leaflets are mounted to the support structure and the coupling means is associated with the support structure. With this in mind, the connection means and the coupling means are configured such that the coupling means engages the connection means to physically dock the replacement prosthetic heart valve to the first prosthetic heart valve following implantation of the first prosthetic heart valve.

DETAILED DESCRIPTION

Figure 1A:
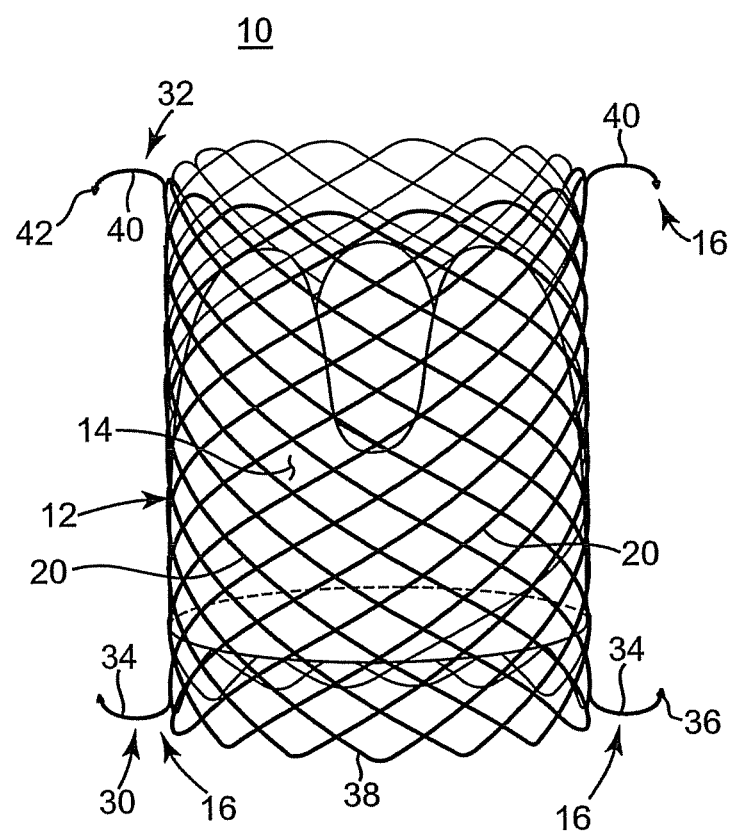
FIG. 1A is a side, perspective view of a prosthetic heart valve in accordance with the present invention.

One embodiment of a prosthetic heart valve 10 in accordance with the present invention is shown in FIG. 1A. The prosthetic heart valve 10 includes a support structure 12, leaflets 14, and coupling means 16 (referenced generally in FIG. 1A). Details on the various components are described below. In general terms, however, the support structure 12 is generally tubular, with the leaflets 14 being secured to an interior of the support structure 12. The coupling means 16 extends radially outwardly relative to the leaflets 14. As described below, the coupling means 16 is adapted to physically dock or connect the prosthetic heart valve 10 to a previously implanted prosthetic heart valve (not shown) to achieve a connective interface between the physical structures of the prosthetic heart valve 10 and the previously implanted prosthetic heart valve apart from and in addition to any interface that may be effectuated by radial press-fitting of the prosthetic heart valve 10 against the previously implanted prosthetic heart valve. As used throughout this specification, the term "prosthetic heart valve" is in reference to a bioprosthetic heart valve or a heart valve configuration utilizing synthetic leaflets, and excludes mechanical heart valves characterized as having a mechanically coupled, metal occluding disk or leaflet structure.

The support structure 12 is, in one embodiment, a wire stent capable of transitioning from a collapsed state to an expanded state (shown in FIG. 1A). In one embodiment, individual wires 20 comprising the support structure 12 are formed of a metal or other material that facilitates folding of the support structure 12 to a contracted state in which an internal diameter defined by the support structure 12 is greatly reduced from an internal diameter in the expanded state. Thus, for example, in the collapsed state, the support structure 12 can be mounted over a delivery device, such as a balloon catheter, as described below. Alternatively, the wires 20 can be formed from a shape memory material such as a nickel titanium alloy (NiTi or Nitinol®). With this configuration, the support structure 12 is self-transitionable from the contracted state to the expanded state, such as by the application of heat, energy, etc.

As described in greater detail below, the prosthetic heart valve 10 is, following an implantation procedure, physically docked to a previously implanted prosthetic heart valve (not shown). With this in mind, a longitudinal length and diameter of the support structure 12 in the expanded state is related to the previously implanted prosthetic heart valve to which the prosthetic heart valve 10 is applied. Thus, the support structure 12 can assume a variety of different longitudinal lengths and/or diameters. In one embodiment, for example, the support structure 12 has a longitudinal length in the expanded state that is slightly greater than a length of the previously implanted prosthetic heart valve, and a free-standing outer diameter that is greater than an inner diameter of the previously implanted prosthetic heart valve. With this one embodiment, upon transitioning toward the expanded state, the support structure 12 presses against an inner diameter of the previously implanted prosthetic heart valve. With the one embodiment of FIG. 1A, the support structure 12 defines a right cylinder in the expanded state. However, as described in greater detail below, other shapes are equally acceptable. For example, portions of the support structure 12 can define an enlarged diameter as compared to other portions. Further, depending upon the previously implanted heart valve being functionally replaced, the support structure 12 can be less uniform along a longitudinal length thereof, such as when functionally replacing a Freestyle™ bioprosthetic tissue valve available from Medtronic, Inc., or similar prosthetic heart valve whereby the support structure 12 wall can be cut away.

Figure 1B:
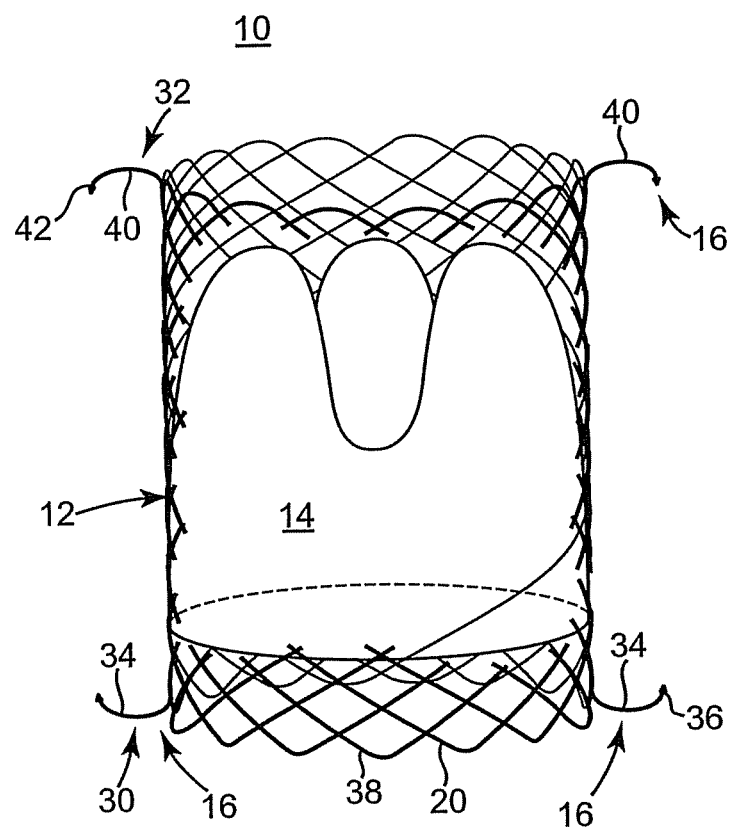
FIG. 1B is a side view of the prosthetic heart valve of FIG. 1A, with portions removed to better illustrate interior leaflets.

The leaflets 14 are secured to an interior of the support structure 12. FIG. 1B better illustrate this relationship, whereby portions of the wires 20 are removed from the drawing. The leaflets 14 can be formed from a variety of materials, such as autologous tissue, xenograph material, or synthetics as are known in the art. With the embodiment of FIGS. 1A and 1B, the leaflets 14 are provided as a homogenous, biological valve structure, such as a porcine, bovine, or equine valve.

Alternatively, the leaflets 14 can be provided independent of one another (e.g., bovine or equine pericardial leaflets) and subsequently assembled to the support structure 12. Further, while three of the leaflets 14 are illustrated in FIGS. 1A and 1B, the prosthetic heart valve 10 of the present invention can incorporate more or fewer leaflets than three.

In more general terms, the combination support structure 12/leaflets 14 can assume a variety of other configurations varying from that shown and described, including any known prosthetic heart valve design. In one embodiment, the support structure 12/leaflets 14 is any known expandable prosthetic heart valve configuration, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", *Pediatric Cardiology,* 2002; 39:1664-1669; Anderson HR, et al., "Transluminal Implantation of Artificial Heart Valves", *EUR Heart J.,* 1992; 13:704-708; Anderson, J. R., et al., "Transluminal Catheter Implantation of New Expandable Artificial Cardiac Valve", *EUR Heart J.,* 1990, 11: (Suppl) 224a; Hilbert S. L., "Evaluation of Explanted Polyurethane Trileaflet Cardiac Valve Prosthesis", J *Thorac Cardiovascular Surgery,* 1989; 94:419-29; Block PC, "Clinical and Hemodyamic Follow-Up After Percutaneous Aortic Valvuloplasty in the Elderly", *The American Journal of Cardiology,* Vol. 62, Oct. 1, 1998; Boudjemline, Y., "Steps Toward Percutaneous Aortic Valve Replacement", *Circulation,* 2002; 105: 775-558; Bonhoeffer, P., "Transcatheter Implantation of a Bovine Valve in Pulmonary Position, a Lamb Study", *Circulation,* 2000:102:813-816; Boudjemline, Y., "Percutaneous Implantation of a Valve in the Descending Aorta In Lambs", *EUR Heart J,* 2002; 23:1045-1049; Kulkinski, D., "Future Horizons in Surgical Aortic Valve Replacement: Lessons Learned During the Early Stages of Developing a Transluminal Implantation Technique", *ASAIO J.* 2004; 50:364-68; the teachings of all of which are incorporated herein by reference. Thus, the support structure 12 can include other features, not specifically described or shown, apart from the coupling means 16. In an alternative embodiment, the support structure 12 has a non-expandable design, but is sized and shaped to nest within a previously implanted heart valve (not shown) in a manner that presses features of the previously implanted heart valve (e.g., leaflets) outwardly relative to the native conduit.

Regardless of the exact configuration of the support structure 12 and leaflets 14, the coupling means 16 is connected to, or formed as part of, the support structure 12 and, in one embodiment, includes an inflow section 30 and an outflow section 32. With the one embodiment of FIG. 1A, the inflow section 30 consists of a plurality of discrete anchors 34 formed as extensions of individual ones of the wires 20 otherwise comprising the support structure 12. Alternatively, the anchors 34 can be separately formed and attached to the support structure 12. As described in greater detail below, the inflow anchors 34 are configured to engage a sewing ring (not shown) of a previously implanted prosthetic heart valve (not shown). Alternatively, the inflow anchors 34 can be configured to engage other structure(s) of the previously implanted prosthetic heart valve. With this in mind, in one embodiment each of the inflow anchors 34 has a hook-like shape and terminates in a barbed end 36. The curvature associated with each of the inflow anchors 34 is such that the respective barbed ends 36 extend inwardly relative to an inflow end 38 of the support structure 12.

The outflow section 32 similarly includes, with the one embodiment of FIG. 1A, a plurality of outflow anchors 40 each in the form of a hook terminating in a barbed end 42. As described in greater detail below, each of the outflow anchors 40 are adapted to project around the stent structure (not shown) associated with a previously implanted prosthetic heart valve (not shown), with the respective barbed ends 42 engaging within material associated with that stent structure. Thus, with the one embodiment of FIG. 1A, the radius of curvature associated with the outflow anchors 40 is less than a radius of curvature associated with the inflow anchors 34. Alternatively, the anchors 40 can be configured the physically dock with other structure(s) provided by the previously implanted heart valve.

Any number of the inflow anchors 34 and/or the outflow anchors 40 can be provided with the prosthetic heart valve 10 of the present invention, and preferably correlates with the previously implanted prosthetic heart valve. Further, the anchors 34, 40 can assume a variety of forms that are or are not identical, such as barbs, clips, staples, hooks, etc. Also, while the anchors 34, 40 are illustrated as extending from opposing ends, respectively, of the support structure 12, alternatively, the anchors 34 and/or 40 can be intermediately disposed along a longitudinal length of the support structure 12.

Figure 1C:
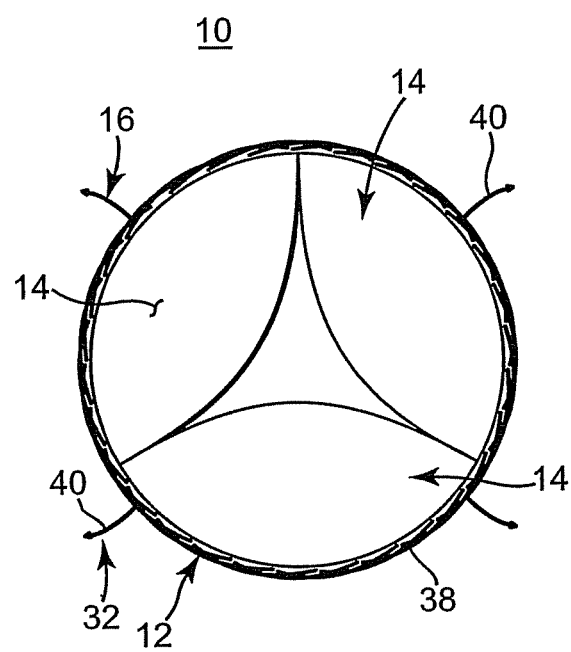
FIG. 1C is an end view of the prosthetic heart valve of FIG. 1A.

With additional reference to FIG. 1C, the prosthetic heart valve 10 is constructed by securing the leaflets 14 to an interior periphery of the support structure 12. To this end, a wide variety of attachment techniques can be employed. For example, the leaflets 14 can be sewn to the support structure 12. Alternatively, other coupling techniques, such as crimping, adhesive, etc., can be employed. The coupling means 16 are similarly secured to the support structure 12 extending radially outwardly relative to the leaflets 14. As a point of reference, FIG. 1C illustrates the outflow section 32 of the coupling means 16. Regardless, the coupling means 16 or portions thereof, can be integrally or homogenously formed with the support structure 12. Alternatively, the coupling means 16, or portions thereof, can be separately formed and assembled to the support structure 12. In one embodiment, construction and/or attachment of the coupling means 16 is such that in the expanded state of the support structure 12 (FIGS. 1A-1C), the coupling means extends radially outwardly, whereas in the contracted state (not shown), the coupling means 16 is retracted.

Figure 2A:
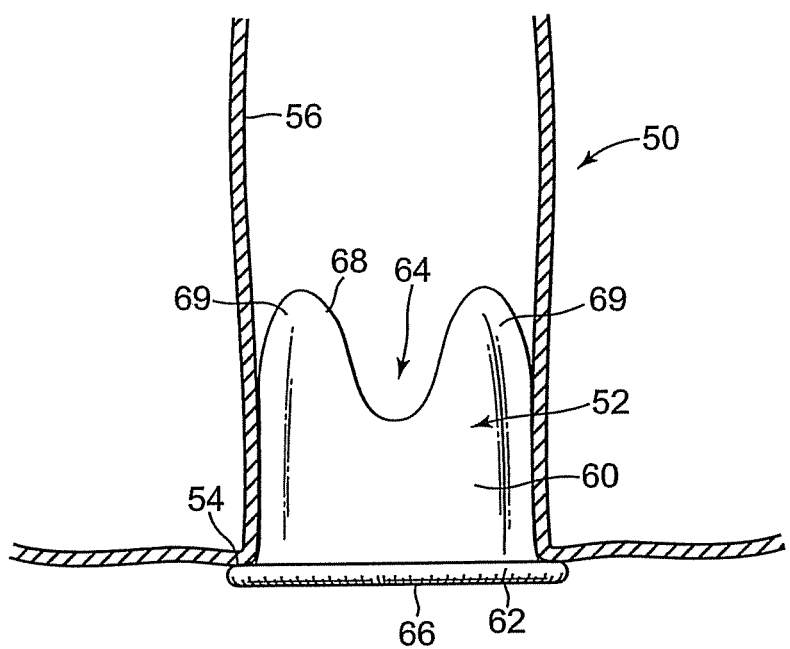
FIGS. 2A-2C illustrate percutaneous deployment of the prosthetic heart valve of FIG. 1A within a previously implanted prosthetic heart valve.

The prosthetic heart valve 10 of the present invention is uniquely adapted to facilitate an implantation technique whereby the prosthetic heart valve 10 is mounted to a previously implanted prosthetic heart valve. By way of reference, FIG. 2A illustrates, in simplified form, a native heart valve 50 of a patient to which a previously implanted prosthetic heart valve 52 has been secured. The native heart valve 50 can be any of the human heart valves (i.e., mitral valve, tricuspid valve, aortic valve, or pulmonary valve), it being understood that the type and orientation of the previously implanted prosthetic heart valve 52 will correspond with the particular form, shape, and function of the native heart valve 50. Regardless, the native heart valve 50 defines a valve annulus or valvular rim 54 from which a lumen 56 defined by the native heart valve 50 extends.

The previously implanted prosthetic heart valve 52 is, in one embodiment, any known prosthetic heart valve or valved conduit, and thus can assume a variety of forms. In most general terms, the previously implanted prosthetic heart valve 52 includes a valve structure 60 connected to a sewing ring 62. The valve structure 60 may or may not include an internal stent, but is generally tubular in form, defining an internal region 64 (referenced generally) extended from an inflow end 66 to an outflow end 68. With the exemplary embodiment of FIG. 2A, the previously implanted prosthetic heart valve 52 includes stent posts 69 (for example, a biological, aortic or mitral prosthetic heart valve including a stent with three commissure posts), it being understood that the prosthetic heart valve of the present invention can be employed to functionally replace stentless prosthetic heart valves as well. Relative to the view of FIG. 2A, the internal region 64 is essentially encompassed by the valve structure 60, it being understood that the valve structure 60 selectively allows for fluid flow into or out of the lumen 56 of the natural heart valve 50; thus, the internal region 64 is openable to the lumen 56. For ease of illustration, leaflets associated with the previously implanted prosthetic heart valve 52 are not shown in FIG. 2A. Regardless, the previously implanted prosthetic heart valve 52 has been implanted via accepted surgical techniques, whereby the sewing ring 62 is sewn or attached to the annulus 54 of the native heart valve 50.

At some time following implant, it may be discovered that the previously implanted prosthetic heart valve 52 is functionally deficient due to one or more of a variety of factors, such as stenosis, valve failure, inflammation, native valve insufficiency, etc. Regardless, rather than removing the previously implanted prosthetic heart valve 52 and implanting a second, similarly formed prosthetic heart valve via rigorous open heart surgical techniques, the method of the present invention leaves the previously implanted prosthetic heart valve 52 in place, and deploys the prosthetic heart valve 10 (FIG. 1A) onto the previously implanted prosthetic heart valve 52.

Figure 2B:
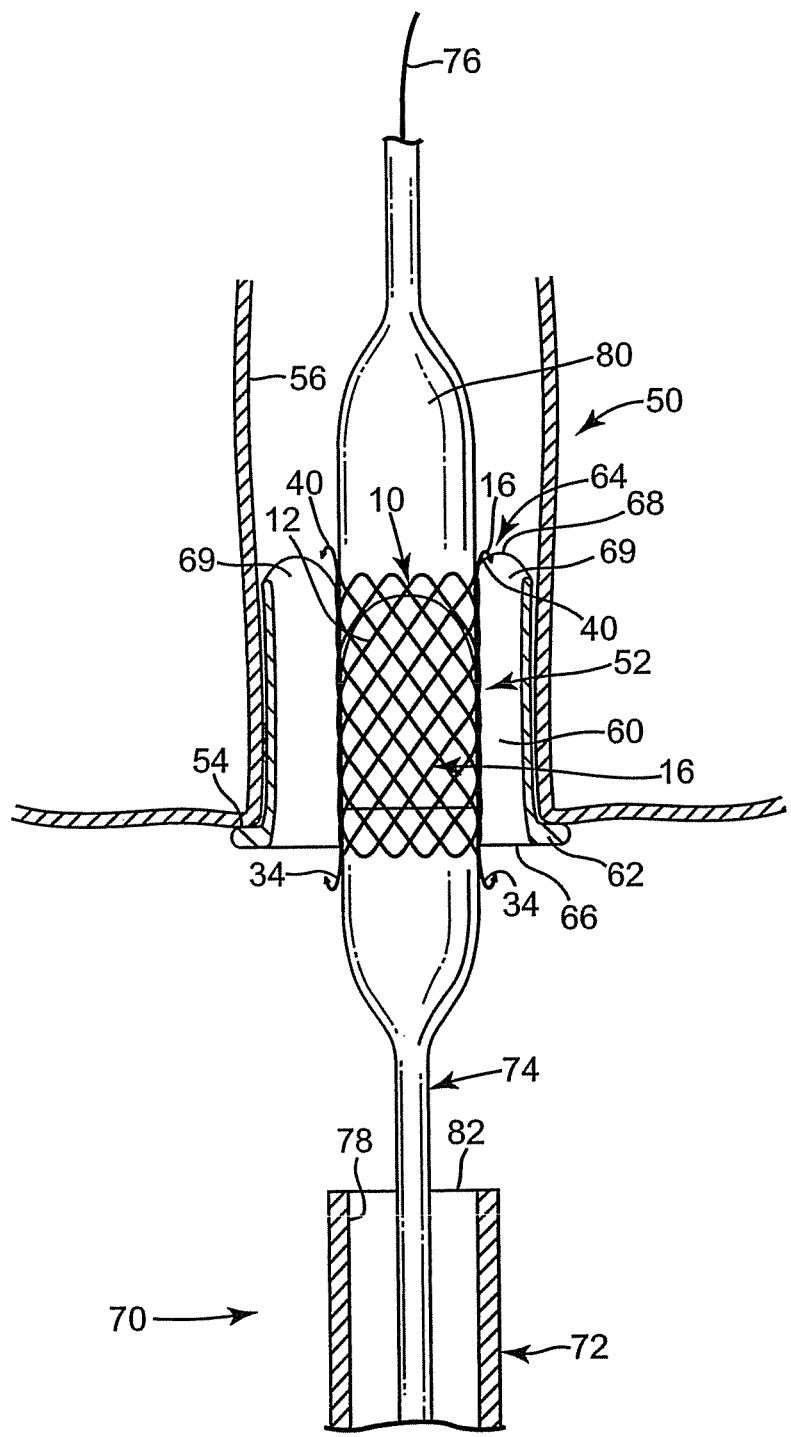

In one embodiment, the prosthetic heart valve 10 is delivered to the native heart valve 52 percutaneously, as represented in simplified form in FIG. 2B. In general terms, a transcatheter assembly 70 is provided, including a delivery catheter 72, a balloon catheter 74, and a guide wire 76. The delivery catheter 72 is of a type known in the art, and defines a lumen 78 within which the balloon catheter 74 is received. The balloon catheter 74, in turn, defines a lumen (not shown) within which the guide wire 76 is slidably disposed. Further, the balloon catheter 74 includes a balloon 80 that is fluidly connected to an inflation source (not shown). The transcatheter assembly 70 is appropriately sized for a desired percutaneous approach to the native heart valve 50. For example, the transcatheter assembly 70 can be sized for delivery to the native heart valve 50 via an opening at a carotid artery, a jugular vein, a sub-clavian vein, femoral artery or vein, etc. Essentially, any percutaneous intercostals penetration can be made to facilitate use of the transcatheter assembly 70.

With the above in mind, prior to delivery, the prosthetic heart valve 10 is mounted over the balloon 80 in a contracted state as shown in FIG. 2B. As compared to the expanded state of FIG. 1A, the support structure 12 is compressed onto itself and the balloon 80, thus defining a decreased inner diameter (as compared to an inner diameter in the expanded state). Further, the coupling means 16, including the inflow and outflow anchors 34, 40, are retracted in the contracted state (as compared to an extended orientation of the coupling means 16 in the expanded state of FIG. 1A).

With the prosthetic heart valve 10 mounted to the balloon 80, the transcatheter assembly 70 is delivered through a percutaneous opening (not shown) in the patient via the delivery catheter 72. The native heart valve 50 is located by extending the guide wire 76 from a distal end 82 of the delivery catheter 72, with the balloon catheter 74 otherwise retracted within the delivery catheter 72. In this regard, the guide wire 76 passes through the internal region 64 defined by the previously implanted prosthetic heart valve 52.

Once the native heart valve 50 has been located, the balloon catheter 74 is advanced distally from the delivery catheter 72 along the guide wire 76, with the balloon 80/prosthetic heart valve 10 positioned relative to the previously implanted heart valve 52 as shown in FIG. 2B. More particularly, the balloon 80/prosthetic heart valve 10 is positioned within the internal region 64 of the previously implanted prosthetic heart valve 52, with the inflow anchors 34 positioned adjacent the inflow end 66/sewing ring 62 of the previously implanted prosthetic heart valve 52, whereas the outflow anchors 40 are positioned adjacent the outflow end 68 of the previously implanted prosthetic heart valve 52. In an alternative embodiment, the prosthetic heart valve 10 is delivered to the previously implanted prosthetic heart valve 52 via a minimally invasive surgical incision (non-percutaneously). In another alternative embodiment, the prosthetic heart valve 10 is delivered via open heart/chest surgery. Regardless, with the prosthetic heart valve 10 in the contracted state, the support structure 12 readily moves within the internal region 64 of the previously implanted prosthetic heart valve 52, and the coupling means 16, which is otherwise retracted, does not unintentionally contact or engage portions of the previously implanted prosthetic heart valve 52. In one embodiment, the prosthetic heart valve 10 includes a radiopaque material to facilitate visual confirmation of proper placement of the prosthetic heart valve 10 relative to the previously implanted prosthetic heart valve 52. Alternatively, other known surgical visual aids can be incorporated into the prosthetic heart valve 10.

Figure 2C:
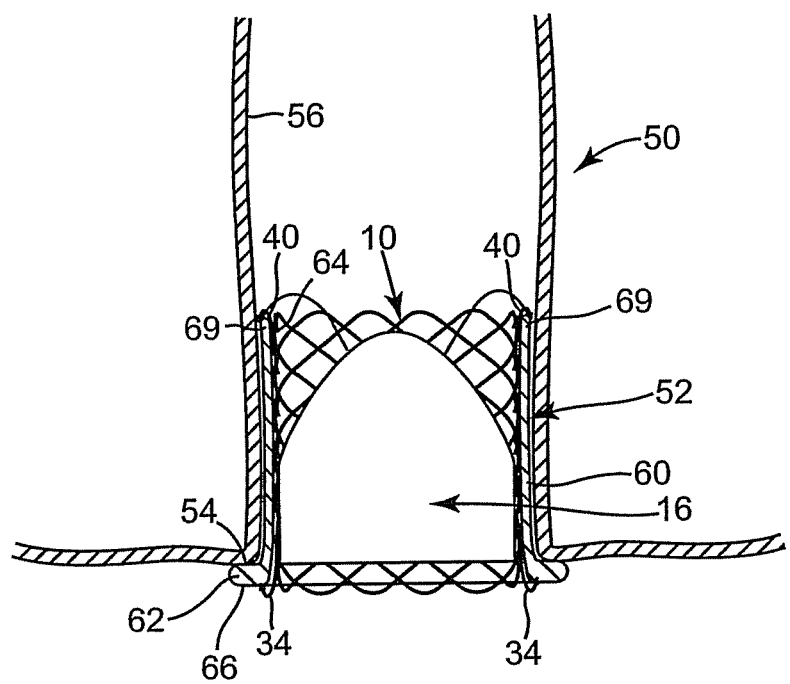

Once the prosthetic heart valve 10 is properly positioned, the balloon catheter 74 is operated to inflate the balloon 80, thus transitioning the prosthetic heart valve 10 to the expanded state as shown in FIG. 2C. As a point of reference, the transcatheter assembly 70 is removed from the view of FIG. 2C. Alternatively, where the support structure 12 is formed of a shape memory material, the prosthetic heart valve 10 self-transitions to the expanded state of FIG. 2C (and thus can be percutaneously delivered by an appropriate catheter device other than a balloon catheter). Similarly, with an alternative configuration, the prosthetic heart valve 10 can be unfurled to the expanded state, again without the assistance of a balloon catheter. Regardless, the support structure 12 expands within the internal region 64 of the previously implanted heart valve 52, radially pressing against the valve structure 60. To this end, where the previously implanted prosthetic heart valve 52 includes leaflets (not shown), radial expansion of the support structure 12 presses against these leaflets, lodging them against the valve structure 60.

With the prosthetic heart valve 10 in the expanded state, the coupling means 16 physically docks or connects the prosthetic heart valve 10 to the previously implanted prosthetic heart valve 52. For example, as shown in FIG. 2C, the inflow anchors 34 lodge within the sewing ring 62 of the previously implanted prosthetic heart valve 52, such as via the barbed end 36 (FIG. 1A) associated with each of the inflow anchors 34. The outflow anchors 40 wrap around the outflow end 68 of the previously implanted prosthetic heart valve 52, with the corresponding barbed ends 42 lodging within an outer fabric therein. For example, each of the outflow anchors 40 wraps about a corresponding stent post 69 of the previously implanted prosthetic heart valve 52. Notably, the physical docking or connection between the coupling means 16 and the previously implanted heart valve 52 is apart from, or in addition to, any frictional, radial interface between the prosthetic heart valve 10 and the previously implanted heart valve 52 otherwise achieved by radial force or pressure exerted by the support structure 12 against the previously implanted heart valve 52 in the expanded state.

With the above-described technique, the prosthetic heart valve 10 serves as a functional replacement for the previously implanted prosthetic heart valve 52, utilizing the sewing ring 62 of the previously implanted prosthetic heart valve 52 as a platform for securement relative to the native heart valve 50. That is to say the sewing ring 62 of the previously implanted heart valve 52 has previously been sutured to the annulus or valvular rim 56 of the native heart valve 50; by fastening the prosthetic heart valve 10 to the sewing ring 62, no additional suturing is required. Following fastening of the prosthetic heart valve 10 to the previously implanted prosthetic heart valve 52, the leaflets 14 (one of which is shown in FIG. 2C) serve as replacement valve leaflets, facilitating normal functioning of the native heart valve 50.

Attachment of the prosthetic heart valve 10 to the previously implanted prosthetic heart valve 52 can be accomplished in a variety of fashions other than that described with respect to the one embodiment of prosthetic heart valve 10 described above. For example, the coupling means 16 need not include inflow and outflow sections, but instead can be directly, physically docked to the previously implanted prosthetic heart valve 52 at only one end thereof. Further, while the coupling means 16 has been described as including hooks with barbed ends, other anchoring techniques can be employed whereby the anchors do not necessarily pierce through the previously implanted prosthetic heart valve 52 material. To this end, clip(s), staple(s), or other fastening devices can be employed.

Figure 3:
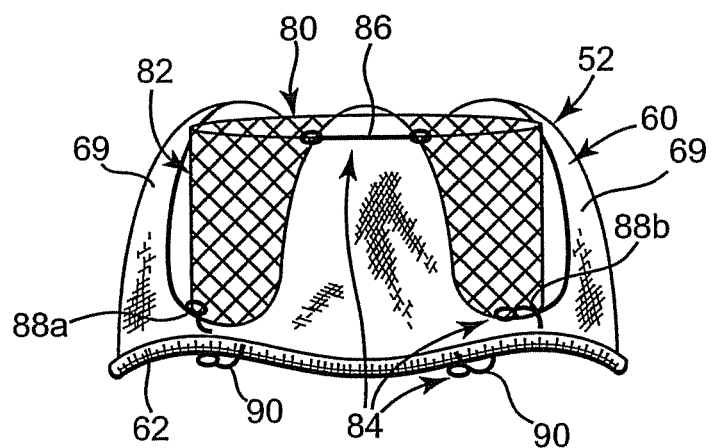
FIG. 3 is a side perspective view of an alternative embodiment prosthetic heart valve in accordance with the present invention physically docked or connected to a previously implanted prosthetic heart valve.

For example, an alternative embodiment prosthetic heart valve 80 internally positioned and physically docked or connected to a previously implanted prosthetic heart valve 52 is shown in FIG. 3. The prosthetic heart valve 80 includes a support structure 82, leaflets (not shown) and coupling means 84 (referenced generally). In general terms, the support structure 82 and the leaflets can assume any of the forms previously described with respect to the prosthetic heart valve 10 (FIGS. 1A-1C) previously described. With the embodiment of FIG. 3, the coupling means 84 includes an outflow anchor 86, intermediate anchors 88*a*, 88*b*, and inflow anchors 90. As described below, each of the anchors 86-90 can achieve physical docking or connection of the prosthetic heart valve 80 to the previously implanted heart valve 52, such that one or more of the features 86-90 can be eliminated. Alternatively, or in addition, the coupling means 84 can include components not specifically shown in FIG. 3.

In one embodiment, the outflow anchor 86 is a clasp or hook formed as part of the support structure 82 at the outflow end thereof. For example, the support structure 82 can be a wire-formed stent, with an individual wire being bent, or two wires combined, to form the outflow anchor 86. The outflow anchor 86 is generally sized and shaped in accordance with an expected size and shape of a stent post 69 of the previously implanted prosthetic heart valve 52 for reasons described below. To this end, the outflow anchor 86 can be the result of normal manufacture techniques for forming a stent-type support structure. During implantation, the prosthetic heart valve 80 is positioned, in a contracted state, within the previously implanted prosthetic heart valve 52 with the outflow anchor 86 located beyond the previously implanted prosthetic heart valve 52, and in particular the stent posts 69. The prosthetic heart valve 80 is then transitioned to an expanded state (shown in FIG. 3). Once expanded, the prosthetic heart valve 80 is retracted relative to the previously implanted prosthetic heart valve 52 such that the outflow anchor 86 slides over one of the stent posts 69, thereby physically docking or connecting the prosthetic heart valve 80 to the previously implanted prosthetic heart valve 52. In one embodiment, the outflow anchor 86 is sized and shaped so as to readily clear a leading end of the stent post 69, but will more firmly dock or connect to the stent post 69 at an intermediate section thereof that is otherwise wider and/or thicker than the leading end. Where the previously implanted prosthetic heart valve 52 includes an internal wire frame (not shown) traversing an outflow periphery thereof (e.g., Carpentier-Edwards Bioprostheses, available from Edwards Lifescience), a more rigid physical docking or connection can be achieved. While the prosthetic hart valve 80 is illustrated in FIG. 3 as including a single outflow anchor 86, alternatively two or more of the outflow anchors 86 can be provided.

The intermediate anchors 88*a*, 88*b* are, in one embodiment, hooks or barbs, and extended generally radially outwardly from the support structure 82 at a location(s) between the opposing ends thereof. To this end, the intermediate anchors 88*a*, 88*b* are located to physically dock or connect to portions of the previously implanted prosthetic heart valve 52 at points other than leading ends of the stent posts 69. For example, the intermediate anchor 88*a* is configured and positioned to pierce into material of the previously implanted prosthetic heart valve 52 (such as between adjacent stent posts 69 and/or along a length of one of the stent posts 69) upon transitioning of the prosthetic heart valve 80 to the expanded state. In one embodiment, the intermediate anchor 88*a* pierces through an interior of the previously implanted prosthetic heart valve 52. The intermediate anchor 88*b*, on the other hand, is configured and positioned to wrap about and contact an area of the previously implanted prosthetic heart valve 52 between adjacent ones of the stent posts 69 with the prosthetic heart valve 80 in the expanded state.

Where the previously implanted prosthetic heart valve 52 includes an internal wire frame (not shown) traversing an outflow periphery thereof (e.g., Carpentier-Edwards Bioprostheses, available from Edwards Lifescience), a more rigid physical docking or connection can be achieved. For example, the intermediate anchor 88*a* extends immediately below (relative to the orientation of FIG. 3), and thus braces against the internal wire frame. Additionally, the intermediate anchor 88*b* extends immediately above (relative to the orientation of FIG. 3), and thus braces against, the internal wire frame. In alternative embodiments, more or less of the intermediate anchors 88*a*, 88*b* can be provided as compared to the one embodiment illustrated in FIG. 3.

In one embodiment, the inflow anchors 90 are hooks or barbs extending from the support structure 82, although a variety of other constructions are also acceptable. Regardless, the inflow anchors 90 are constructed to facilitate physical docking or connection to the sewing ring 62 of the previously implanted prosthetic heart valve 52.

Figure 4A:
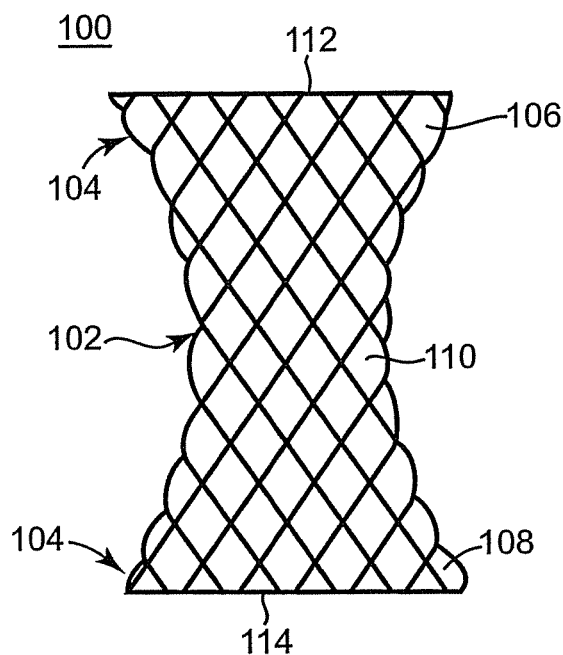
FIG. 4A is a side view of an alternative embodiment prosthetic heart valve in accordance with the present invention.

In addition or as an alternative to the coupling means described above, the support structure of the prosthetic heart valve can, in and of itself, be adapted to facilitate physical docking or connection to the previously implanted prosthetic heart valve 52. For example, an alternative embodiment prosthetic heart valve 100 in accordance with the present invention is shown in FIG. 4A. The prosthetic heart valve 100 is similar to the prosthetic heart valve 10 (FIG. 1A) previously described, and is adapted to functionally replace a previously implanted prosthetic heart valve (not shown). With this in mind, the prosthetic heart valve 100 includes a support structure 102, leaflets (not shown), and coupling means 104. With the one embodiment of FIG. 4A, the support structure 102 is a tubular, wire stent and defines, in the expanded state of FIG. 4A, opposing first and second end portions 106, 108 and an intermediate portion 110. The leaflets are similar to the leaflets 14 (FIG. 1A) previously described and are interiorly secured to the support structure 102 along the intermediate portion 110. As made clear below, the first and second end portions 106, 108 serve as the coupling means 104.

In particular, the support structure 102 is constructed such that in the expanded state of FIG. 4A, the first and second end portions 106, 108 define an increased outer diameter as compared to the intermediate portion 110. For example, the first end portion 106 increases in diameter from the intermediate portion 110 to a first end 112. Similarly, the second end portion 108 increases in diameter from the intermediate portion 110 to a second end 114. Alternatively, other shapes can be defined, and only one of the first or second end portions 106, 108 need define the increased diameter in the expanded state. Regardless, a maximum diameter defined by one or both of the first and second end portions 106, 108 corresponds with a diameter of a previously implanted prosthetic heart valve (not shown in FIG. 4A), with the maximum diameter being greater than a diameter of the previously implanted prosthetic heart valve. The support structure 102 need not assume the hourglass-like shape of FIG. 4A in a contracted state (not shown), but instead can be a substantially right cylinder amenable for delivery to a target site. Transition to the expanded state can be achieved in a variety of fashions, such as by an appropriately devised balloon catheter (e.g., a balloon catheter having three balloon sections inflatable to different outer diameters), or by employing a shape memory material for the support structure 102.

Figure 4B:
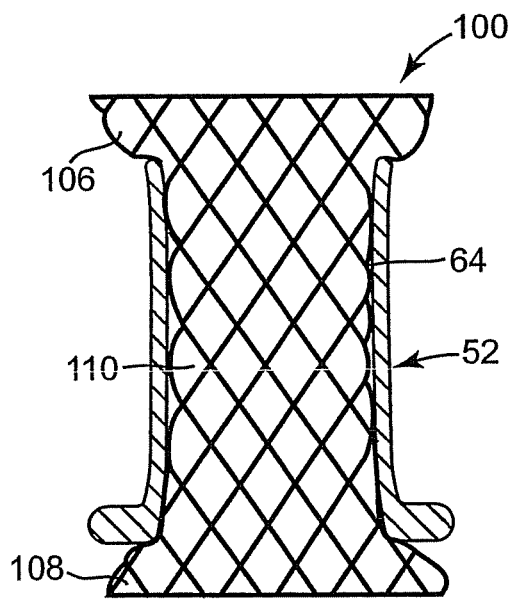
FIG. 4B is a side view of the prosthetic heart valve of FIG. 4A mounted to a previously implanted prosthetic heart valve.

Regardless of exact construction, the prosthetic heart valve 100 is delivered in the contracted state, according to the techniques previously described. In particular, and with reference to FIG. 4B, the prosthetic heart valve 100 is positioned within the internal region 64 of the previously implanted prosthetic heart valve 52 (it being understood that in the view of FIG. 4B, the prosthetic heart valve 100 has been transitioned to the expanded state). Once properly positioned, the prosthetic heart valve 100 is transitioned to the expanded state, with the first and second end portions 106, 108 assuming the increased outer diameter as compared to the intermediate section 110. Once again, the support structure 102 presses against the previously implanted prosthetic heart valve 52 that is otherwise secured to the native heart valve 50 (FIG. 2A). Once in the expanded state, the coupling means 104 (i.e., the first and second end portions 106, 108) nest about the previously implanted prosthetic heart valve 52, thereby physically docking or connecting the prosthetic heart valve 100 to the previously implanted prosthetic heart valve 52. Notably, the coupling means 104 associated with FIGS. 4A and 4B can be used alone or in conjunction with the coupling means 16 (FIG. 1A) previously described.

Regardless of exact form, the coupling means associated with the prosthetic heart valve of the present invention need not effectuate a rigid, locking engagement with the previously implanted prosthetic heart valve 52. In fact, depending upon the exact form of the previously implanted prosthetic heart valve, effectuating a rigid engagement may be difficult. In more general terms, however, the coupling means associated with the prosthetic heart valve of the present invention is capable of remaining physically docked or connected to the previously implanted prosthetic heart valve 52 under back-pressure conditions of at least 200 mHg.

Figure 5:
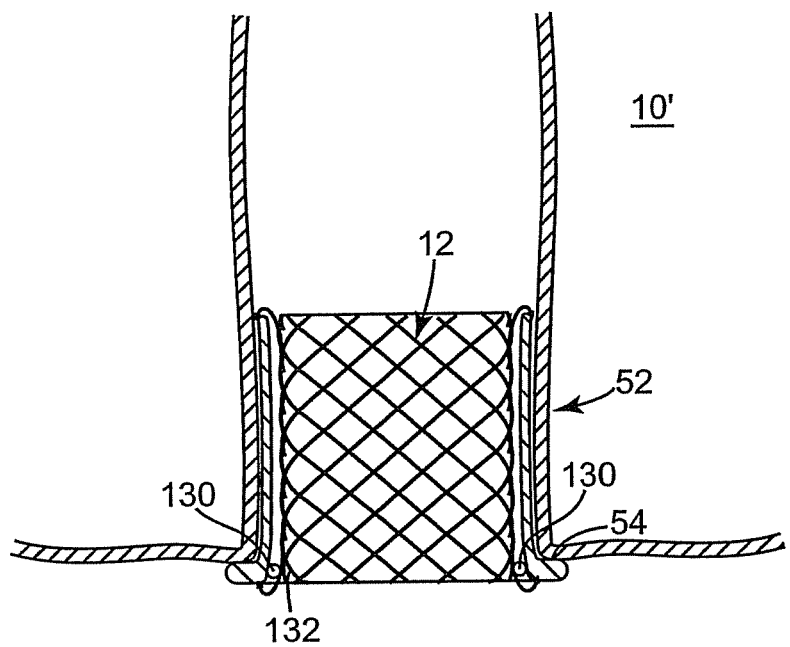
FIG. 5 is a side, cross-sectional view of an alternative embodiment prosthetic heart valve physically connected or docked to a previously implanted prosthetic heart valve.

To ensure a sealing relationship between the prosthetic heart valve 10, 100, and the previously implanted prosthetic heart valve 52, in an alternative embodiment, a gasket material can be provided as shown, for example, at 130 in FIG. 5. As a point of reference, FIG. 5 depicts the previously implanted prosthetic heart valve 52 in conjunction with an alternative embodiment prosthetic heart valve 10' that is highly similar to the prosthetic heart valve 10 (FIG. 1A) previously described and further includes the gasket material 130. The gasket material 130 is, in one embodiment, attached to an outer circumference of the support structure 12 at or adjacent an annulus portion 132 that is otherwise expected to be positioned adjacent the annulus or valvular rim 54 of the previously implanted prosthetic heart valve 52. Alternatively, the gasket material 130 can encompass a more significant exterior length of the support structure 12. Regardless, the gasket material 130 can be made from fabric, felt, Teflon®, silicone, pericardium, or other polymeric or biological materials. As shown in FIG. 5, the gasket material 130 serves as a filler to prevent holes from forming between the prosthetic heart valve 10' and the previously implanted prosthetic heart valve 52 adjacent the annulus or valvular rim 54, thus preventing leaching of blood back through this region.

Figure 6A:
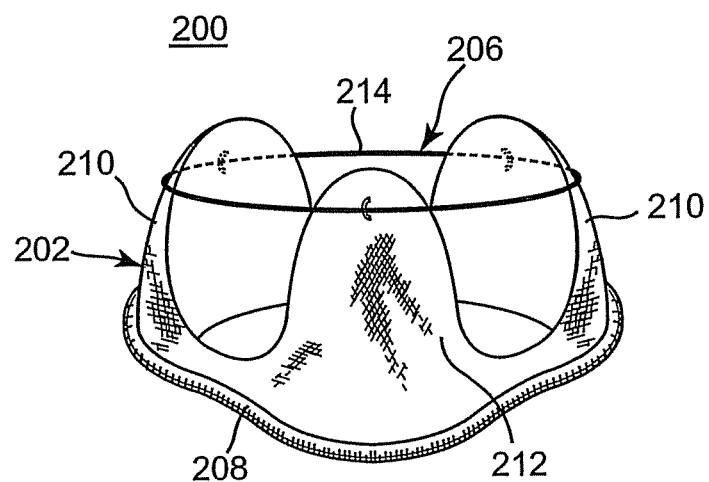
FIG. 6A is a side, perspective view of a prosthetic heart valve adapted to couple with a replacement prosthetic heart valve in accordance with the present invention.

In addition to, in one embodiment, providing the prosthetic heart valve 10 (FIG. 1A) with coupling means adapted to achieve physical docking or connection with a previously implanted prosthetic heart valve, in other embodiments, the present invention includes providing the previously implanted prosthetic heart valve with features that further facilitate the desired physical docking or connection. In this context, it is possible to reference the initial, first implanted prosthetic heart valve as a "first implanted prosthetic heart valve" and the subsequently implanted, functional replacement prosthetic heart valve (e.g., the prosthetic heart valve 10 of FIG. 1A) as a "replacement prosthetic heart valve". With these definitions in mind, FIG. 6A illustrates one embodiment of a first implanted prosthetic heart valve 200 in accordance with the present invention. The first implanted prosthetic heart valve 200 can assume a variety of forms, but generally includes a support structure 202, leaflets (not shown), and connection means 206. The support structure 202 maintains the leaflets and facilitates attachment of the prosthetic valve 200 to a native heart valve (not shown). The connection means 206 is connected to, or formed by, the support structure 202, and promotes physical docking or connection of a replacement prosthetic heart valve (not shown, but for example, the prosthetic heart valve 10 of FIG. 1A) to the first prosthetic heart valve 200.

In the one embodiment of FIG. 6A, the support structure 202 defines a sewing ring 208 and includes a stent (hidden) forming stent posts 210 and encompassed by a covering 212, such as with a Medtronic® Hancock II® or Musiac® stented tissue valve. A wide variety of other stented tissue valves, such as those described in U.S. Pat. Nos. 4,680,031, 4,892,541, and 5,032,128, the teachings of which are incorporated herein by reference, can be employed as the support structure 202. Alternatively, the support structure 202 can be stentless, such as, for example, with a Freestyle® stentless bioprosthesis, available from Medtronic, Inc. Other acceptable stentless configurations are described in U.S. Pat. Nos. 5,156,621; 5,197,979; 5,336,258; 5,509,930; 6,001,126; 6,254,436; 6,342,070; 6,364,905; and 6,558,417, the teachings of all of which are incorporated herein by reference, to name but a few. Regardless, the leaflets (not shown) are attached to the support structure 202 (e.g., by sewing, crimping, adhesive, etc.), and can assume a variety of forms (autologous tissue, xenograph tissue, or synthetic material).

With the general construction of the support structure 202/leaflets in mind, the connection means 206 associated with the embodiment of FIG. 6A includes a wire ring 214 extending between the stent posts 210 (either adjacent the leading (or outflow) ends thereof as illustrated, or more closely positioned to the sewing ring 208). The wire ring 214 can be fastened to the support structure 202 in a variety of manners, including, for example, sewing the wire ring 214 to the fabric covering 212. While the wire ring 214 is illustrated as being a single, continuous structure, in an alternative embodiment, two or more individual wire segments are provided and secured to the support structure, with the segments combining to define a continuous or discontinuous ring-like structure 202. Regardless, the wire ring 214 is positioned so as to not interfere with functioning/movement of the leaflets adjacent an outflow (or inflow) end of the first prosthetic heart valve 200.

Figure 6B:
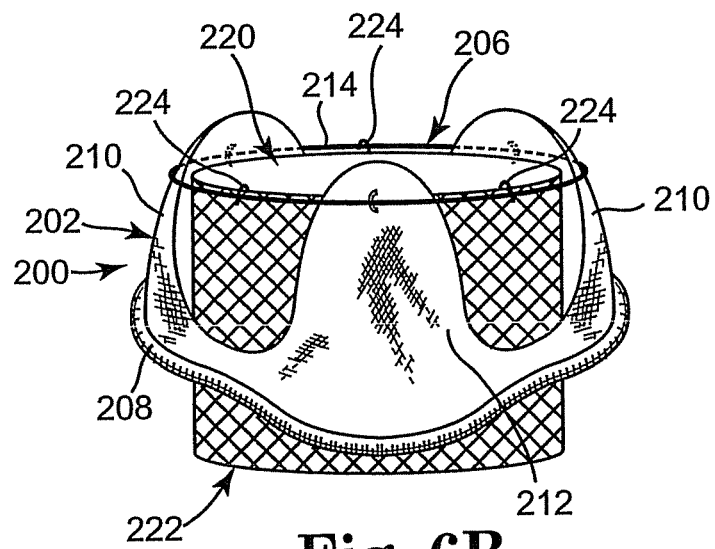
FIG. 6B is a side view of a replacement prosthetic heart valve physically docked or connected to the prosthetic heart valve of FIG. 6A.

With further reference to FIG. 6B, the connection means 206, and in particular the wire ring 214, is adapted to promote physical docking or connecting of a replacement prosthetic heart valve 220 to the first prosthetic heart valve 200. By way of reference, the replacement prosthetic heart valve 220 is akin to the prosthetic heart valve 10 (FIG. 1A) previously described, and includes a support structure 222 and a coupling means in the form of outflow anchors or hooks 224. With this in mind, the first prosthetic heart valve 200 is initially implanted in a patient (not shown) and secured to native tissue (not shown), for example via the sewing ring 208. When desired, the first prosthetic heart valve 200 can be functionally replaced by the replacement prosthetic heart valve 220. More particular, the replacement prosthetic heart valve 220 can be delivered and positioned in a contracted state within the first prosthetic heart valve 220 pursuant to any of the techniques previously described. The replacement prosthetic heart valve 220 then transitions to the expanded state (shown in FIG. 6B), thereby deploying the coupling means or outflow hooks 224. The replacement prosthetic heart valve 220 is then maneuvered such that the hooks 224 engage the wire ring 214, thereby physically docking or connecting the replacement prosthetic heart valve 220 to the first prosthetic heart valve 200. Alternatively, the replacement prosthetic heart valve 220 can include differing coupling means, such as a detent, for capturing or physically connecting to the wire ring 214.

Figure 7:
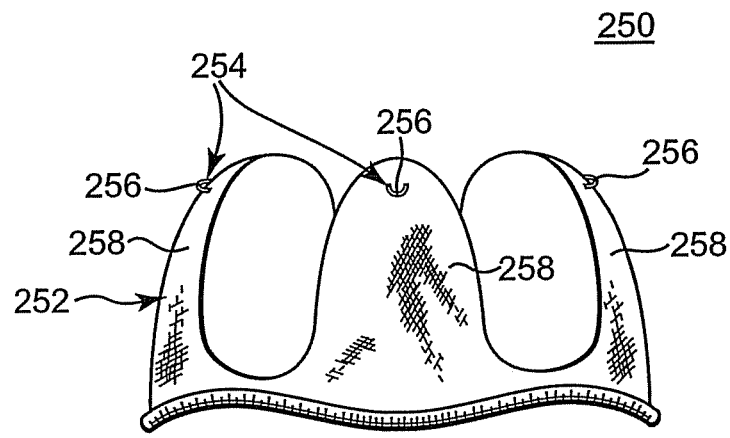
FIG. 7 is a side view of an alternative embodiment prosthetic heart valve.

The connection means 206 associated with the first prosthetic heart valve 200 can assume a number of other configurations. For example, FIG. 7 illustrates an alternative embodiment first prosthetic heart valve 250 including a support structure 252, leaflets (not shown), and connection means 254 (referenced generally). The support structure 252 and the leaflets can assume any of the forms previously described. The connection means 254 includes a plurality of rings 256, respective ones of which extend from individual stent posts 258. Each of the rings 256 preferably extends in a radially outward fashion relative to the corresponding stent post 258, and is longitudinally open relative to a central axis defined by the support structure 252. Following initial implant, the first prosthetic heart valve 250 can be functionally replaced by a replacement prosthetic heart valve (not shown, but akin to the prosthetic heart valve 10 of FIG. 1A) by physically docking or connecting the coupling means (e.g., hooks) of the replacement prosthetic heart valve within the rings 256.

Figure 8:
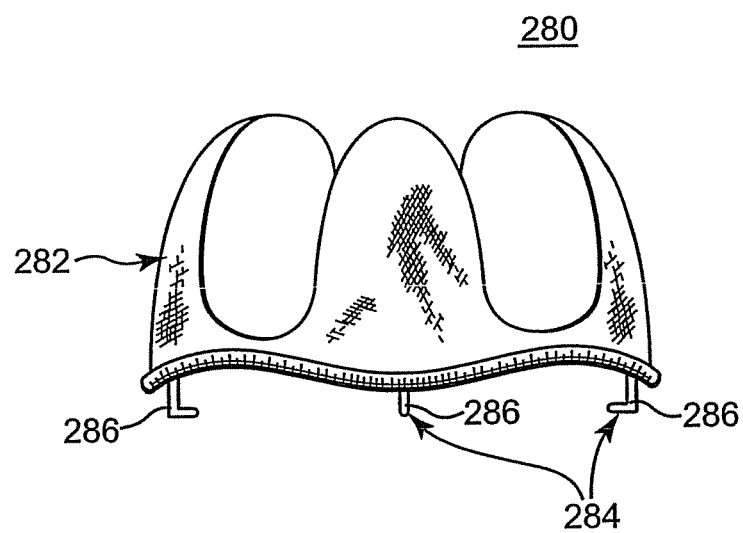
FIG. 8 is a side view of an alternative embodiment pros ethic heart valve.

Yet another alternative embodiment first prosthetic heart valve 280 in accordance with the present invention is shown in FIG. 8 and includes a support structure 282, leaflets (not shown) and connection means 284 (referenced generally). The support structure 282 and the leaflets can assume any of the forms previously described. The connection means 284 is attached to, or formed by, the support structure 282 and includes a plurality of protrusions 286. With the one embodiment of FIG. 8, the protrusions 286 are hooks, although other configurations, such as posts, barbs, eyelets, etc., are equally acceptable. Regardless, the protrusions are positioned, in one embodiment, at an inflow side of the prosthetic heart valve 280, and are adapted to facilitate physical docking or connection with a corresponding coupling means or feature (e.g., post, hook, eyelet, etc.) of a replacement prosthetic heart valve (not shown) following a procedure to functionally replace the first prosthetic heart valve 280.

Figure 9A:
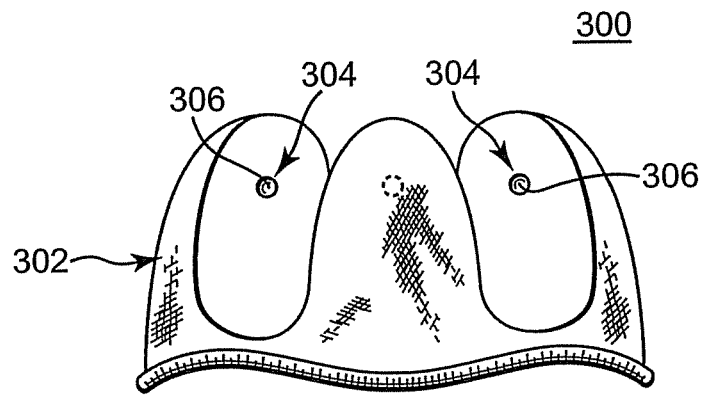
FIG. 9A is a side, perspective view of a prosthetic heart valve adapted to couple with a replacement prosthetic heart valve in accordance with the present invention.
Figure 9B:
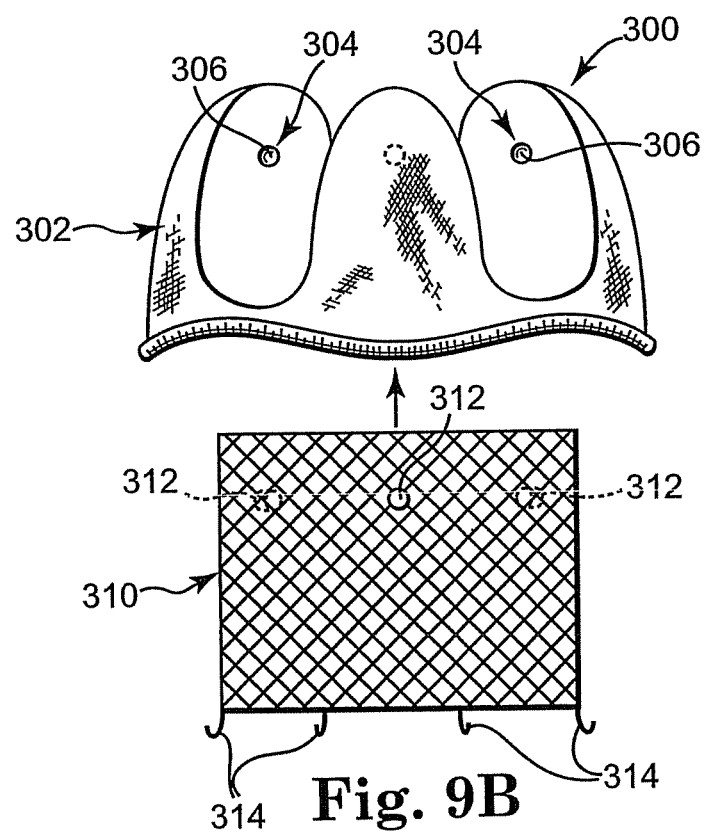
FIG. 9B is a side view of a replacement prosthetic heart valve physically docking or connecting to the prosthetic heart valve of FIG. 9A.

Yet another alternative embodiment first prosthetic heart valve 300 in accordance with the present invention is shown in FIG. 9A and includes a support structure 302, leaflets (not shown), and connection means 304 (referenced generally). The support structure 302 and the leaflets can assume any of the forms previously described. The connection means 304 is formed by the support structure 302 and, with the embodiment of FIG. 9A, includes a plurality of apertures 306 (shown generally in FIG. 9A). During a procedure to functionally replace the first prosthetic heart valve 300 with a replacement prosthetic heart valve 310 and as shown in FIG. 9B, the apertures 306 are sized to capture corresponding tabs 312 provided by the replacement prosthetic heat valve 310, thus physically docking or connecting the replacement prosthetic heart valve 310 to the first prosthetic heart valve 300. Further, with the one embodiment of FIG. 9B, additional coupling means 314 (e.g., barbed hooks) are provided with the replacement prosthetic heart valve 310 and also physically dock or connect to the first prosthetic heart valve 300.

Figure 10A:
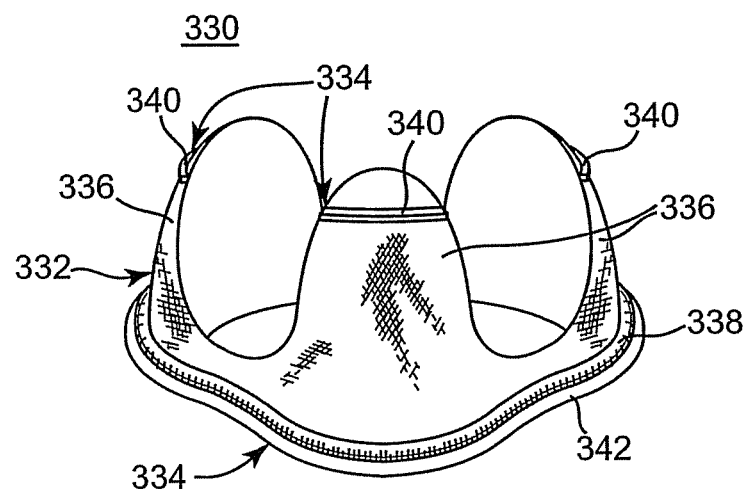
FIG. 10A is a side, perspective view of a prosthetic heart valve adapted to couple with a replacement prosthetic heart valve in accordance with the present invention.
Figure 10B:
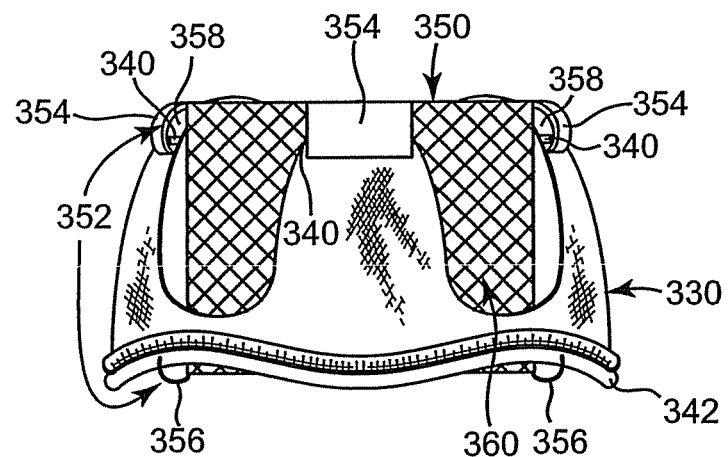
FIG. 10B is a side view of a replacement prosthetic heart valve physically docked or connected to the prosthetic heart valve of FIG. 10A.

Yet another alternative embodiment first prosthetic heart valve 330 is shown in FIG. 10A and includes a support structure 332, leaflets (not shown) and connection means 334 (referenced generally). The support structure 332 and the leaflets can assume any of the forms previously described, with the support structure 332 including stent posts 336 and a sewing ring 338. The connection means 334 is connected to, or formed by, the support structure 332 and includes, with the one embodiment of FIG. 10A, a plurality of outflow ribs 340 and an inflow rib 342. Respective ones of the outflow ribs 340 extend radially outwardly relative to respective ones of the stent posts 336 and are positioned along a length thereof, in one embodiment adjacent a leading end of the respective stent post 336. The inflow rib 342 is contiguous with, and extends axially from, the sewing ring 338. The connection means 334 is configured to facilitate physical docking or connection of a replacement prosthetic heart valve, such as the replacement valve 350 as shown in FIG. 10B. In one embodiment, the replacement prosthetic heart valve 350 has coupling means 352 (referenced generally) including tabs 354 and protrusions 356. The tabs 354 define capture slots 358 relative to a support structure 360 of the replacement prosthetic heart valve 350. Following a functional replacement procedure, the outflow ribs 340 are lodged within the capture slots 358 (formed, for example, by corresponding recess and radial extension features), and the protrusions 356 engage the inflow rib 342.

The embodiments of FIGS. 6A-10B above are but a few examples of combination first prosthetic heart valve/replacement prosthetic heart valve configurations in accordance with the present invention. In other alternative embodiments, the first prosthetic heart valve includes a magnetic material (such as internal, magnetic ring) whereas the replacement prosthetic heart valve includes a magnetic material connected to or provided as part of its support structure. Virtually any magnetic material could be employed, such as ferrous or ferritic materials, rare earth magnetic materials such as Neodymium (Nd—Fe—B) and Samarium cobalt magnets (SmCo), etc. During use, the replacement prosthetic heart valve is magnetically attracted to the magnetic material of the first prosthetic heart valve, thus facilitating physical docking or connection to the first prosthetic heart valve. In more general terms, the first prosthetic heart valve and the corresponding replacement valve are configured to provide complimentary features that promote physical docking or connection of the replacement prosthetic heart valve to the first prosthetic heart valve as part of a procedure to functionally replace the first prosthetic heart valve. To this end, the complimentary first prosthetic heart valve and replacement prosthetic heart valve can be packaged together and sold as a kit.

The prosthetic heart valve and related method of implantation presents a marked improvement over previous designs. In particular, by utilizing a previously implanted prosthetic heart valve as a platform to facilitate mounting relative to a native heart valve, the prosthetic heart valve of the present invention is highly amenable to percutaneous delivery. Further, by functionally replacing a previously implanted prosthetic heart valve, the deficient prosthetic heart valve need not be physically removed from the patient. Thus, the prosthetic heart valve and related method of implantation of the present invention can be used at any point during the "useful life" of a conventional prosthetic heart valve. Further, the methodology associated with the present invention can be repeated multiple times, such that several prosthetic heart valves of the present invention can be mounted on top of or within one another.

Although the present invention has been described with reference to preferred embodiments, workers skilled in the art will recognize that changes can be made in form and detail without departing from the spirit and scope of the present invention.

What is claimed is:

1. A prosthetic heart valve for functionally replacing a previously implanted prosthetic heart valve, the prosthetic heart valve comprising:
   a collapsible support structure, the support structure having an axial length terminated by an inflow end and an outflow end;
   leaflets directly mounted to the support structure; and
   coupling means directly mounted to the support structure, the coupling means including a radially outwardly extending first anchor disposed on the inflow end and a radially outwardly extending second anchor on the outflow end, wherein the first anchor includes a first radius of curvature and the second anchor includes a second radius of curvature, and wherein the first radius of curvature is less than the second radius of curvature.

2. The prosthetic heart valve of claim 1, wherein the support structure is a stent.

3. The prosthetic heart valve of claim 2, wherein the stent is transitionable from a collapsed state to an expanded state having an enlarged diameter as compared to the collapsed state.

4. The prosthetic heart valve of claim 2, wherein the coupling means is attached to the stent.

5. The prosthetic heart valve of claim 2, wherein the prosthetic heart valve is configured such that an exterior of the stent is exposed along an entirety of the length.

6. The prosthetic heart valve of claim 1, wherein the coupling means is adapted to retract radially in a collapsed state and extend radially in an expanded state.

7. The prosthetic heart valve of claim 1, wherein the leaflets are formed from a material selected from the group consisting of autologous tissue, xenograph material, and synthetic.

8. The prosthetic heart valve of claim 1, wherein the coupling means extends radially outwardly relative to the leaflets.

9. The prosthetic heart valve of claim 1, further comprising:
   a gasket material mounted to an exterior of the support structure.

10. A prosthetic heart valve for functionally replacing a previously implanted prosthetic heart valve, the prosthetic heart valve comprising:
    a collapsible support structure having an axial length terminated by an inflow end and an outflow end;
    leaflets directly mounted to the support structure; and
    a plurality of anchors directly mounted to the support structure, the plurality of anchors including a radially outwardly extending first anchor disposed on the inflow end and a radially outwardly extending second anchor on the outflow end, wherein the first anchor includes a first radius of curvature and the second anchor includes a second radius of curvature, and wherein the first radius of curvature is less than the second radius of curvature.

* * * * *